US009800853B2

(12) United States Patent
D'Alfonso et al.

(10) Patent No.: US 9,800,853 B2
(45) Date of Patent: Oct. 24, 2017

(54) ADAPTIVE CAMERA WHITE BALANCE SYSTEM AND METHOD

(71) Applicant: Arthrex, Inc., Naples, FL (US)

(72) Inventors: David D'Alfonso, Gaviota, CA (US); Craig Speier, Santa Barbara, CA (US); Bruce Laurence Kennedy, Santa Barbara, CA (US)

(73) Assignee: ARTHREX, INC., Naples, FL (US)

( * ) Notice: Subject to any disclaimer, the term of this patent is extended or adjusted under 35 U.S.C. 154(b) by 351 days.

(21) Appl. No.: 14/717,974

(22) Filed: May 20, 2015

(65) Prior Publication Data

US 2016/0344992 A1 Nov. 24, 2016

(51) Int. Cl.
*H04N 9/73* (2006.01)
*A61B 1/00* (2006.01)
*A61B 1/04* (2006.01)
*H04N 5/225* (2006.01)
*A61B 1/06* (2006.01)
(Continued)

(52) U.S. Cl.
CPC ......... *H04N 9/735* (2013.01); *A61B 1/00006* (2013.01); *A61B 1/00096* (2013.01); *A61B 1/04* (2013.01); *A61B 1/05* (2013.01); *A61B 1/0661* (2013.01); *A61B 1/0669* (2013.01); *A61B 1/07* (2013.01); *H04N 5/2256* (2013.01); *H04N 5/2354* (2013.01); *H04N 9/045* (2013.01); *H04N 2005/2255* (2013.01); *H04N 2209/041* (2013.01)

(58) Field of Classification Search
CPC .... H04N 9/735; H04N 5/2256; H04N 5/2354; H04N 9/045; A61B 1/0661; A61B 1/0669; A61B 1/07
See application file for complete search history.

(56) References Cited

U.S. PATENT DOCUMENTS

| 5,319,449 A | * | 6/1994 | Saito | H04N 9/735 348/223.1 |
| 5,325,185 A | * | 6/1994 | Tsuchiva | H04N 9/735 348/207.99 |

(Continued)

FOREIGN PATENT DOCUMENTS

CN 102068228 5/2011

OTHER PUBLICATIONS

Int'l. Search Report and the Written Opinion, dated Jul. 20, 2016.

*Primary Examiner* — Mishawn Hunter
(74) *Attorney, Agent, or Firm* — Karish & Bjorgum, PC

(57) ABSTRACT

A method for color correction in a camera system having a camera, a light source and a controller, the method comprising: setting a first light source drive current level; performing a first white balance operation and obtaining at least one of red gain, blue gain and green gain values corresponding to the first light source drive current level; setting a second light source drive current level different than the first light source drive current level; performing a second white balance operation and obtaining at least one of red gain, blue gain and green gain values corresponding to the second light source drive current level; and determining a relationship between light source current levels and at least one of red gain, blue gain and green gain values using the obtained at least one of red gain, blue gain and green gain values corresponding to the first and second light source drive current levels.

17 Claims, 3 Drawing Sheets

(51) Int. Cl.
*H04N 5/235* (2006.01)
*H04N 9/04* (2006.01)
*A61B 1/05* (2006.01)
*A61B 1/07* (2006.01)

(56) References Cited

U.S. PATENT DOCUMENTS

| | | |
|---|---|---|
| 6,665,007 B1 * | 12/2003 | Usami ................... H04N 5/238 |
| | | 348/221.1 |
| 7,262,765 B2 | 8/2007 | Brown et al. |
| 8,690,765 B2 | 4/2014 | Takasugi et al. |
| 8,937,652 B2 | 1/2015 | Ariyoshi et al. |
| 2006/0098108 A1 * | 5/2006 | Kurosawa .......... H04N 1/00397 |
| | | 348/272 |
| 2008/0129847 A1 * | 6/2008 | Kobayashi ........... H04N 5/3728 |
| | | 348/243 |
| 2009/0192351 A1 | 7/2009 | Nishino |
| 2013/0345517 A1 | 12/2013 | Morimoto et al. |
| 2014/0052004 A1 | 2/2014 | D'Alfonso et al. |
| 2014/0180004 A1 | 6/2014 | Yamashita |
| 2014/0293038 A1 | 10/2014 | Delmonico |

* cited by examiner

ADAPTIVE CAMERA WHITE BALANCE SYSTEM AND METHOD

BACKGROUND OF THE INVENTION

This invention relates generally to endoscopic camera systems and, more particularly, to a system and method for adaptive white balance for endoscopic camera systems.

Endoscopic camera systems are used for seeing inside the body of a patient. A typical endoscopic camera system has an illumination system with a light source for illuminating the inside of a body cavity and a camera for capturing images of that cavity. Endoscopic camera systems are known in which white light emitting diodes ("LED") are used as light sources. Additionally, endoscopic systems are known in which an excitation light source, such as a blue laser emitting diode, is used to excite light from phosphors.

It is desirable to reduce the amount of input power to the illumination system for optimal camera exposure purposes, to limit the heat to a user's hand touching an endoscope and to limit heat generated at the distal tip of the endoscope. It is also desirable to reduce the amount of input power to the illumination system to reduce the size and increase the portability of the endoscope by limiting the use of mains power or substantial battery resources. Accordingly, systems are known in which drive current to a light source is reduced to the minimum possible to still obtain adequate illumination.

However, when the drive current is altered, the illumination source color may shift. For example, a color of emitted light from a white LED becomes more blue as the drive current increases. Additionally, in systems where an excitation light source is used, temperature based variation in the excitation light causes a change in efficiency of light emission from the phosphors, which results in changing volume or chromaticity of the finally produced white light. Moreover, there may be variation in drive current caused color shift among different light sources, even of the same type. Without proper color correction, resulting images may have inaccurate colors, which may make it harder for medical personnel to accurately visualize and treat a patient.

Therefore, a need exists for an improved process for allowing light source current variations while maintaining the color accuracy of the image captured by the camera system that remedies the shortcomings of the prior art.

SUMMARY OF INVENTION

Accordingly, the present invention is directed to an endoscopic camera system having a white balance system that is adaptive to drive current variations.

The present invention, according to an embodiment, is directed to a method for color correction in a camera system having a camera, a light source and a controller, the method comprising: setting a first light source drive current level; performing a first white balance operation and obtaining at least one of red gain, blue gain and green gain values corresponding to the first light source drive current level; setting a second light source drive current level different than the first light source drive current level; performing a second white balance operation and obtaining at least one of red gain, blue gain and green gain values corresponding to the second light source drive current level; and determining a relationship between light source current levels and at least one of red gain, blue gain and green gain values using the obtained at least one of red gain, blue gain and green gain values corresponding to the first and second light source drive current levels.

The first and second light source drive current levels may be selected from the group consisting of 25%, 50%, 75% and 100%. In an additional embodiment, the method further has the steps of: setting a third light source drive current level different than the first light source drive current level and the second light source drive current level; and performing a third white balance operation and obtaining at least one of red gain, blue gain and green gain values corresponding to the third light source drive current level.

In an embodiment, after the step of setting a first light source drive current level the method further comprises the step of waiting a predetermined time. The predetermined time may be at least one video frame. After setting a second light source drive current level, the method may further comprises the step of waiting a predetermined time. The predetermined time may be least one video frame to elapse.

The light source may be a white light emitting diode. In an embodiment, the step of determining a relationship between light source current levels and at least one of red gain, blue gain and green gain values comprises determining a relationship between light source current levels and blue gain values. The method may further comprise the step of generating a light source control table comprising at least one of a red gain value, a blue gain value and a green gain value for each light source drive current level.

In an embodiment, the light source is a white light emitting diode and the step of generating a light source control table comprises generating a blue gain value for each light source drive current level. The method may further comprise the step of receiving a white balance request.

The present invention, according to an embodiment, is also directed to a system for color correction in an endoscopic camera system. The system for color correction has an imaging device for taking images; an illumination system for providing light for the imaging device; a camera control unit that processes images from the imaging device, the camera control unit further comprising: an illumination controller; a processor in communication with the illumination controller; and a memory in communication with the processor.

The camera control unit is configured to receive a white balance request; set a first light source drive current level; perform a first white balance operation and obtain at least one of red gain, blue gain and green gain values corresponding to the first light source drive current level. The camera control unit is further configured to set a second light source drive current level different than the first light source drive current level; perform a second white balance operation and obtain at least one of red gain, blue gain and green gain values corresponding to the second light source drive current level. The camera control unit is further configured to determine a relationship between light source current levels and at least one of red gain, blue gain and green gain values using the obtained at least one of red gain, blue gain and green gain values corresponding to the first and second light source drive current levels. The camera control unit is further configured to store the determined relationship between light source current levels and at least one of red gain, blue gain and green gain values to the memory.

The first light source drive current level and the second light source drive current level may be selected from the group consisting of 25%, 50%, 75% and 100%. The camera control unit may be further configured to set a third light source drive current level different than the first light source drive current level and the second light source drive current level; perform a third white balance operation; and obtain at least one of red gain, blue gain and green gain values corresponding to the third light source drive current level. The light source may be a white light emitting diode and the camera control unit may be further configured to generate a light source control table comprising at least one of a red gain value, a blue gain value and a green gain value for each light source drive current level.

The present invention, according to an additional embodiment, is directed to a method for color correction in a camera system having a camera, a light source and a controller, the method comprising: setting a plurality of different light source drive current levels; performing a white balance operation at each of the plurality of light source drive current levels; obtaining at least one of red gain, blue gain and green gain values corresponding to each of the plurality of light source drive current levels; and determining a relationship between light source current levels and at least one of red gain, blue gain and green gain values.

The method may further comprise the step of generating a light source control table comprising at least one of a red gain value, a blue gain value and a green gain value for each light source drive current level. The light source may be a white light emitting diode. The step of generating a light source control table may include generating a blue gain value for each light source drive current level.

BRIEF DESCRIPTION OF THE DRAWINGS

The features, aspects and advantages of the present invention will become better understood with regard to the following description, appended claims and accompanying figures wherein:

DETAILED DESCRIPTION OF THE PREFERRED EMBODIMENTS

In the following description of the preferred embodiments, reference is made to the accompanying drawings which show by way of illustration specific embodiments in which the invention may be practiced. Wherever possible, the same reference numbers will be used throughout the drawings to refer to the same or like parts. It is to be understood that other embodiments may be utilized and structural and functional changes may be made without departing from the scope of the present invention.

Figure 1:
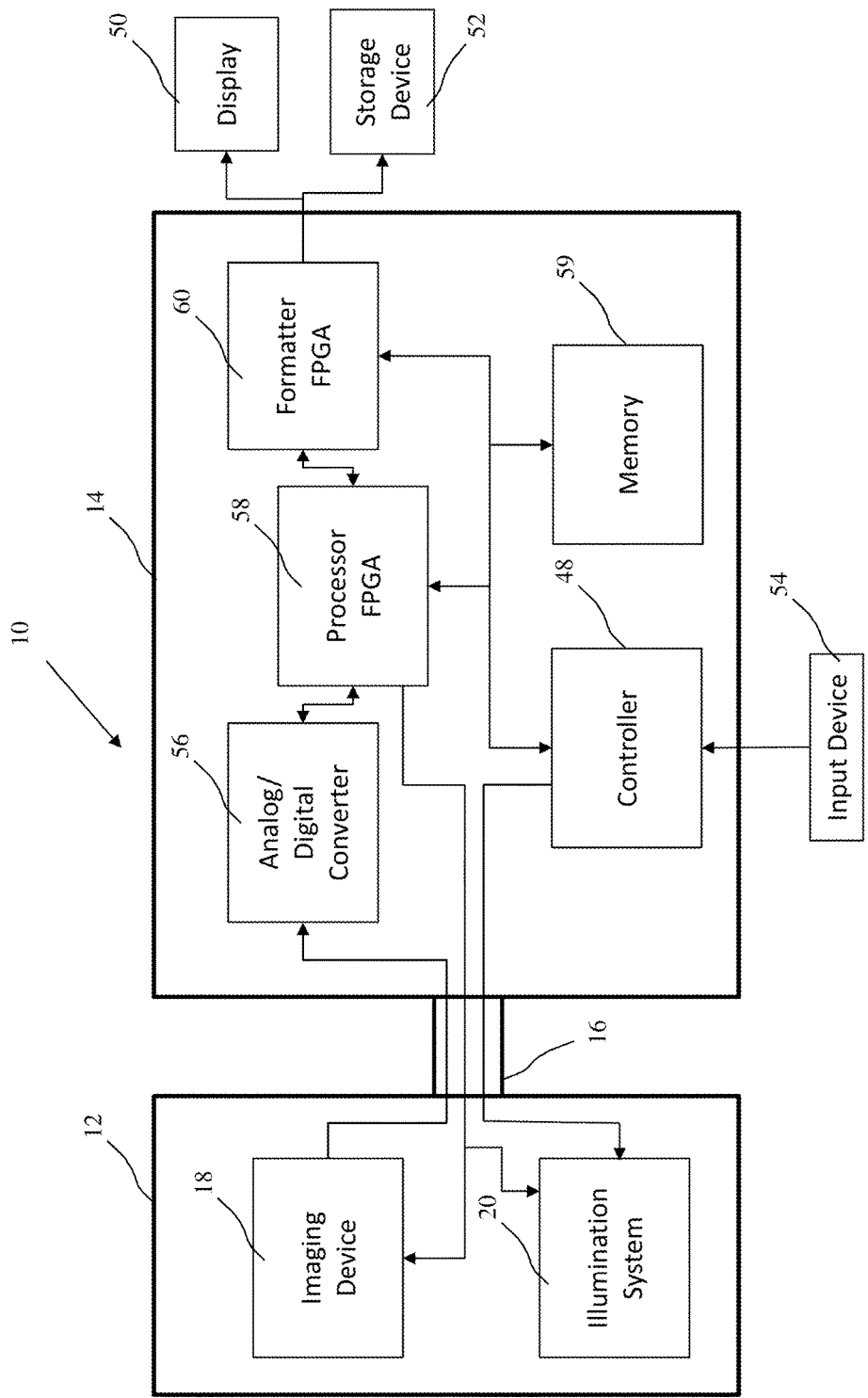
FIG. 1 is a schematic drawing of an endoscope system according to a first embodiment of the present invention.

An endoscopic imaging system 10 according to an embodiment of the present invention is shown in FIG. 1. The endoscopic imaging system 10 allows for internal features of a body of a patient to be viewed without the use of traditional, fully invasive surgery. Additionally, the endoscopy system may be used for imaging of hard to reach parts of structures or in other applications where direct optical viewing is compromised.

The endoscopic imaging system 10 has a camera head 12 and a camera control unit 14. In an embodiment, the camera head 12 is coupled to the camera control unit 14 via a cable 16 to facilitate data transfer between the camera head 12 and the camera control unit 14. In an alternative embodiment, the camera head 12 is wirelessly coupled to the camera control unit 14 such as via IEEE 802.11b, or IEEE 802.11n or ultra-wide band (UWB).

The camera head 12 acquires image data and transmits it to camera control unit 14 to process a usable image. The camera head 12 may be used together with an endoscope or other medical instruments for transmitting image data. The camera head 12 may include one or more imaging devices 18, utilizing a variety of technology types. For example, the imaging devices may include one or more charge coupled device (CCD) sensors or complementary metal-oxide-semiconductor (CMOS) sensors.

Figure 2:
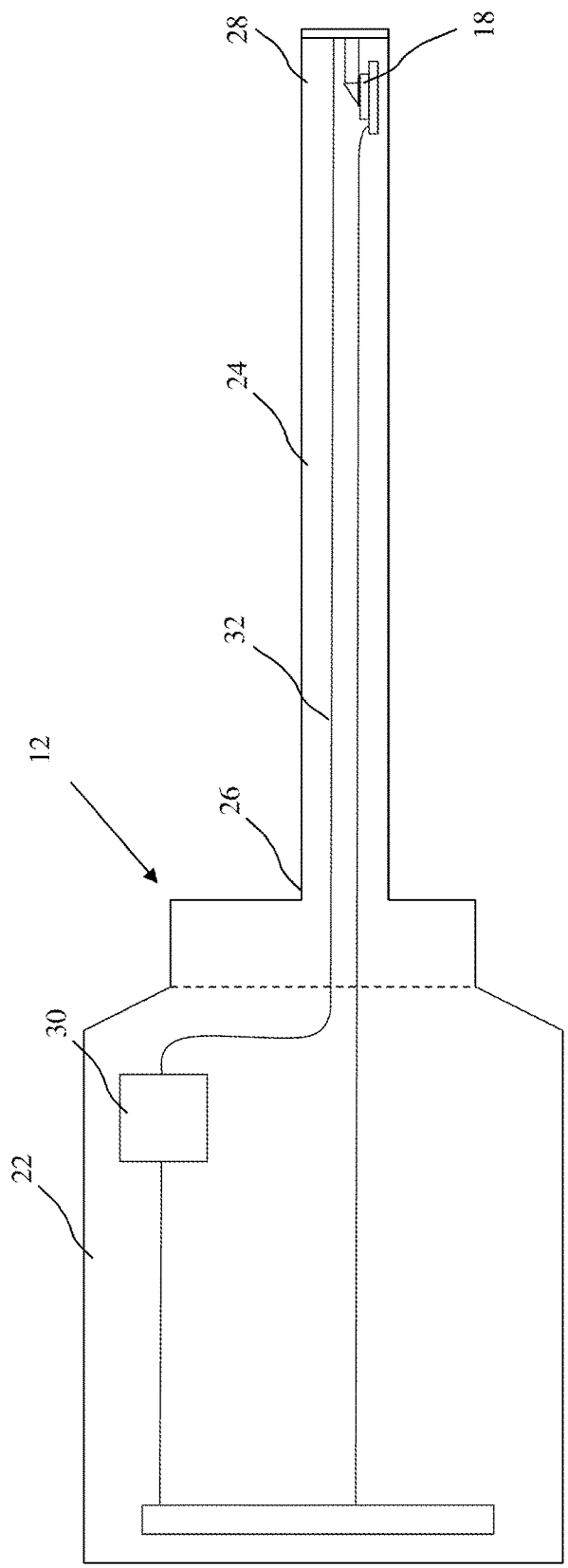
FIG. 2 is a schematic drawing of a camera head usable in the endoscope system of FIG. 1.
Figure 3:
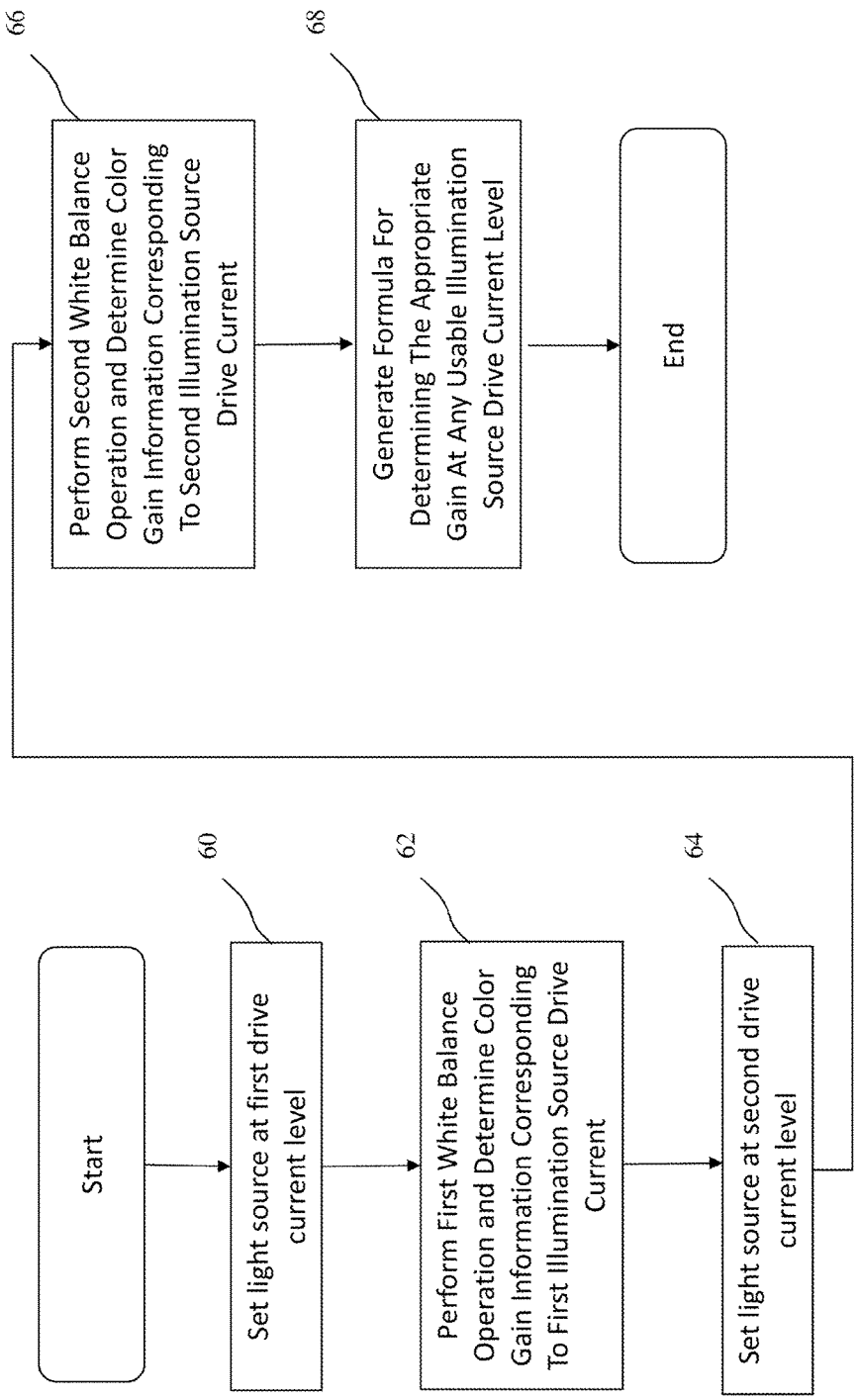
FIG. 3 is a flowchart illustrating a method for color correction in a camera system according to an embodiment of the present invention.

In an embodiment of the present invention, as shown in FIGS. 2 and 3, the camera head 12 has a housing 22 and a shaft 24 coupled to the housing 22. The shaft 24 has a proximal end 26 adjacent to the housing 22 and a distal end 28 for insertion into a body or other area to be viewed. The illumination system includes a light source 30 positioned in the housing 22. In an embodiment, the light source 30 is at least one white light emitting diode ("LED"). A light guide 32 is optically coupled to the light source 30. As will be appreciated by one of skill in the art, optics such as lenses may be placed between the light source 30 and the light guide 32. In an additional embodiment, the light source 30 may be located in the camera control unit 14 and an additional light guide may pass light from the light source in the camera control unit 14 to the light guide 32.

The light guide 32 extends through the shaft 24 to convey light from the light source 30 to near the distal end 28 of the shaft. The light guide 32 is typically formed of optical grade materials, such as acrylic resin, polycarbonate, epoxies and glass. The light guide 32 may terminate near the distal end 28 of the shaft, the exposed end of the light guide polished to pass light out through the distal end of the shaft. Alternatively, near the distal end 28 of the shaft, the light guide 32 may be coupled to a transmission optical assembly 34 that focuses light from the light source and passes the light out through the distal end 28 of the shaft.

Light emitted from the illumination system 20 is applied to an object located outside of the camera head 12. Reflection light comes into the distal end of the shaft 24 and is directed by an imaging optical assembly onto the imaging device 18.

In an additional embodiment of the present invention, the illumination system further comprises at least one additional light source (not shown), such as for infrared and blue illumination for certain fluorescence procedures. These additional light sources, that do not emit light in visible spectrum, may be used in combination with the light source 30 or alone to better differentiate normal from diseased tissue. These additional light sources do not typically affect the drive current based color variation of the light source 30. Accordingly, the white balance system described herein may be used effectively in systems with additional light sources.

The camera control unit 14 will now be explained in more detail with reference to FIG. 1. The camera control unit 14 is preferably a programmable unit containing sufficient processing capacity to accommodate a wide range of control, user interface and image acquisition/processing functions. The camera control unit 14 has a controller 48 and runs program applications providing for a variety of capabilities. For instance, an image capture and display capability allows for both display of a live feed of an image through a display 50 coupled to the camera control unit 14, as well as image capture. Captured images may be stored to an external storage device 52 coupled to the camera control unit 14 such as via a Universal Serial Bus interface. Alternatively, the external storage device 52 may be a storage device accessible via the Internet. Additionally, the controller 48 may receive information and other input from one or more input devices 54.

In an embodiment, analog RGB data is transmitted from the imaging device 18 to the camera control unit 14. The Analog RGB data passes through an Analog/Digital converter 56 to a processor field programmable gate array (FPGA) 58 where the video is processed. The processed video is then passed to a formatter FPGA 60 where the video is formatted into various display formats. The formatter FPGA 60 may also overlay information, such as patient and/or doctor information, onto the video. The formatted video may be converted back to an analog signal for display. The formatted video is sent to the display 50 and/or the storage device 52. Alternatively, an Analog/Digital converter may be located in the camera head and digital RGB data transmitted from the camera head 12 to the camera control unit 14. Additionally, the imaging device 18 itself may include an Analog/Digital converter.

The camera control unit 14 issues commands to the camera head 12 to adjust its operating characteristics, and the camera head 12 may send confirmation to the camera control unit 14 that it received the commands. The processor FPGA 56 and/or the controller 48 may communicate with a shutter driver either in the camera control unit or the camera head to control the exposure period of the imaging device. Additionally, the processor FPGA 56 and/or the controller may communicate with a light source driver either in the camera control unit or the camera head to control the drive current to the illumination source of the illumination system 20.

To correct color temperature shift due to variations in light sources or drive current, the processor FPGA 58 can compensate by adjusting the color balance of the video signal in the camera image processing system such as by adjusting one or more of red gain, green gain and blue gain. The present invention is directed to an improved system and method for calculating necessary color balance.

As part of the normal operation of an endoscope video camera system an initial color adjustment with the intended light source, called "white balance", is performed. To initiate the white balance process, the user aims the camera at a white object and then triggers, with a button press, the automatic selection of color gains to achieve balance. In an embodiment, the white balance operation is performed by setting equal gains for red, green and blue. A sub region of the image is defined, such as a square region of the image that is about 10% of the image height. An average is calculated for each of red, green and blue inside the sub region. The system then determines which of the red, green or blue has the highest average value and set that color to gain=1. The other two color gains are then adjusted so that their average values in the sub region are the same as the highest color.

For example, in a given white balance operation, green may have the highest value within the sub region so the green gain is set at 1. The other colors, red and blue then require gains, such as between 2× and 3× to match G. Once the gains are balanced, the video monitor produces a white color with equal red, green and blue input signals.

In an embodiment of the present invention, the white balance process is expanded to collect color gain information at more than one light source drive current level to form a characterization of light source color behavior at different light source drive current levels. Once the camera controller possesses the relationship between light source drive current and appropriate color gain values, the system can automatically select the color gains for any value of light source drive current to produce accurate color rendition.

In an embodiment, the camera control unit performs two white balance operations, one at 100% light source output and the other at 50% light source output. In this embodiment, it is assumed that there is a roughly linear relationship between drive current and the change in gain needed. However, as will be understood by those of skill in the art, the number of white balance operations may be altered as necessary, such as to account for non-linear relationships between drive current and the change in gain or to otherwise further characterize the relationship between drive current and necessary gain.

For example, three white balance operations may be performed, such as one at 100% light source output, one at 75% light source output and one at 50% light source output. The three data points may be used to establish whether a linear relationship exists between drive current and the change in gain needed. If the relationship between drive current and color change is not determined to be substantially linear, then additional white balance operations may be performed at additional drive current levels to further establish the necessary gain for different output levels. If more than two data points are used, a linear interpolation can be calculated between each data point.

In an embodiment, the white balance is only conducted in relation to one of red gain, green gain and blue gain. In one preferred embodiment, the change in gain necessary to compensate for drive current based changes in color is only assessed for blue gain, because the necessary amount of red gain and green gain will be approximately the same at different LED levels. However, in an embodiment, the change in gain necessary to compensate for drive current based changes in color is assessed for both blue gain and red gain.

As shown in FIG. 3, in an embodiment of the present invention, the white balance method is conducted automatically. A user initiates the white balance process by pointing the camera head 12 at a white object and then pressing a button on the camera head or using the camera control unit input device 54. The camera control unit 14 sets the illumination source drive current at a first level, box 60. In an embodiment, the camera control unit then waits a predetermined time, such as one video frame, to allow the light source temperature to stabilize at the first illumination source drive current. The camera control unit then performs a white balance and determines color gain information corresponding to the first illumination source drive current, box 62. The color gain information corresponding to the first illumination source drive current may be saved in the memory 59 or in a temporary storage.

The camera control unit then sets the illumination source drive current at a second level, different than the first illumination source drive current level, box 64. In an embodiment, the camera control unit then waits a predetermined time, such as one video frame, to allow the light source temperature to stabilize at the second illumination source drive current. The camera control unit then performs a white balance and determines color gain information corresponding to the second illumination source drive current, box 66. The color gain information corresponding to the second illumination source drive current may also be saved in the memory 59 or in a temporary storage.

In additional embodiments, the camera control unit sets the illumination source drive current at one or more additional illumination source drive current levels and determines color gain information corresponding to the one or more additional illumination source drive current levels. The camera control unit 14 saves the color gain information corresponding to the one or more additional illumination source drive current levels and stores the information in the memory 59 or in a temporary storage.

In an additional embodiment of the present invention, the white balances are triggered manually using one or more camera head buttons or using the camera control unit input device 54. A user sets a first illumination source drive current level, then aims the camera head 12 at a white object and triggers a first white balance operation. The camera control unit 14 then determines color gain information corresponding to the first illumination source drive current.

The user sets a second illumination source drive current level different than the first illumination source drive current level, then aims the camera head 12 at a white object and triggers a second white balance operation. The camera control unit 14 then determines color gain information corresponding to the second illumination source drive current. In additional embodiments, the user manually conducts one or more additional white balance operations at different illumination source drive current levels. The camera control unit 14 determines color gain information corresponding to the one or more additional illumination source drive current levels. The color gain information corresponding to the first and second illumination source drive current levels and any additional illumination source drive current levels may be stored in the memory 59 or in temporary storage.

Once the camera control unit 14 has obtained and saved color gain information corresponding to at least two different drive current levels, the camera control unit uses the color gain information to generate a formula for determining the appropriate color gain at any illumination source drive current level, box 68. In an embodiment, the camera control unit 14 generates an additional column in a light source table with at least one color gain value, for example a blue gain value, corresponding to each possible light source drive current level and saves the light source table to the memory 59. In an additional embodiment, the camera control unit 14 saves the color gain formula or the light source table to a memory in the camera head.

In an embodiment, the camera control unit has an LED control table. A column in the LED control table defines the LED fractional output using 12 bits in 0.12 format. From the saved gains corresponding to an LED drive current level of 100% (LED index 319) and an LED drive current level of 50% (LED index 261) a blue gain value is calculated for each LED drive level in the table. The blue gain calibration line slope m=(blue100−blue50)/(1−0.5), where blue100=the blue gain at an LED drive current level of 100% and blue50=the blue gain at an LED drive current level of 50%. Once the slope is calculated, the blue gain at any given LED drive current level may be calculated by the formula:

Blue gain=$m$*(LED fraction−1)+blue100

The blue gain formula may then be used to generate a blue gain value corresponding to each possible LED drive current level and the resulting blue gain values saved as an additional column in the LED control table. An example table follows.

| index | LED dac hex | LED fraction 0.12 binary 12 bit hex |
|---|---|---|
| 0 | 51 | 81 |
| 1 | 52 | 83 |
| 2 | 52 | 84 |
| 3 | 53 | 86 |
| 4 | 54 | 87 |
| 5 | 55 | 89 |
| 6 | 56 | 8A |
| 7 | 57 | 8C |
| 8 | 58 | 8D |
| 9 | 59 | 8F |
| 10 | 5A | 90 |
| 11 | 5B | 92 |
| 12 | 5C | 93 |
| 13 | 5D | 95 |
| 14 | 5E | 97 |
| 15 | 5F | 98 |
| 16 | 60 | 9A |
| 17 | 61 | 9C |
| 18 | 62 | 9D |
| 19 | 63 | 9F |
| 20 | 64 | A1 |
| 21 | 65 | A2 |
| 22 | 66 | A4 |
| 23 | 67 | A6 |
| 24 | 68 | A8 |
| 25 | 69 | AA |
| 26 | 6A | AB |
| 27 | 6B | AD |
| 28 | 6D | AF |
| 29 | 6E | B1 |
| 30 | 6F | B3 |
| 31 | 70 | B5 |
| 32 | 71 | B7 |
| 33 | 72 | B9 |
| 34 | 74 | BB |
| 35 | 75 | BD |
| 36 | 76 | BF |
| 37 | 77 | C1 |
| 38 | 79 | C3 |
| 39 | 7A | C5 |
| 40 | 7B | C8 |
| 41 | 7D | CA |
| 42 | 7E | CC |
| 43 | 7F | CE |
| 44 | 81 | D0 |
| 45 | 82 | D3 |
| 46 | 83 | D5 |
| 47 | 85 | D7 |
| 48 | 86 | DA |
| 49 | 88 | DC |
| 50 | 89 | DE |
| 51 | 8B | E1 |
| 52 | 8C | E3 |
| 53 | 8E | E6 |
| 54 | 8F | E8 |
| 55 | 91 | EB |
| 56 | 92 | ED |
| 57 | 94 | F0 |
| 58 | 95 | F2 |
| 59 | 97 | F5 |
| 60 | 99 | F8 |
| 61 | 9A | FA |
| 62 | 9C | FD |
| 63 | 9E | 100 |
| 64 | 9F | 103 |
| 65 | A1 | 106 |
| 66 | A3 | 108 |
| 67 | A4 | 10B |
| 68 | A6 | 10E |
| 69 | A8 | 111 |
| 70 | AA | 114 |
| 71 | AC | 117 |
| 72 | AD | 11A |
| 73 | AF | 11D |
| 74 | B1 | 120 |
| 75 | B3 | 123 |
| 76 | B5 | 127 |
| 77 | B7 | 12A |

-continued

| index | LED dac hex | LED fraction 0.12 binary 12 bit hex |
|---|---|---|
| 78 | B9 | 12D |
| 79 | BB | 130 |
| 80 | BD | 134 |
| 81 | BF | 137 |
| 82 | C1 | 13A |
| 83 | C3 | 13E |
| 84 | C5 | 141 |
| 85 | C7 | 145 |
| 86 | C9 | 148 |
| 87 | CC | 14C |
| 88 | CE | 150 |
| 89 | D0 | 153 |
| 90 | D2 | 157 |
| 91 | D5 | 15B |
| 92 | D7 | 15E |
| 93 | D9 | 162 |
| 94 | DC | 166 |
| 95 | DE | 16A |
| 96 | E0 | 16E |
| 97 | E3 | 172 |
| 98 | E5 | 176 |
| 99 | E8 | 17A |
| 100 | EA | 17E |
| 101 | ED | 182 |
| 102 | EF | 186 |
| 103 | F2 | 18B |
| 104 | F4 | 18F |
| 105 | F7 | 193 |
| 106 | FA | 198 |
| 107 | FC | 19C |
| 108 | FF | 1A1 |
| 109 | 102 | 1A5 |
| 110 | 105 | 1AA |
| 111 | 108 | 1AE |
| 112 | 10A | 1B3 |
| 113 | 10D | 1B8 |
| 114 | 110 | 1BD |
| 115 | 113 | 1C1 |
| 116 | 116 | 1C6 |
| 117 | 119 | 1CB |
| 118 | 11C | 1D0 |
| 119 | 11F | 1D5 |
| 120 | 122 | 1DB |
| 121 | 126 | 1E0 |
| 122 | 129 | 1E5 |
| 123 | 12C | 1EA |
| 124 | 12F | 1F0 |
| 125 | 133 | 1F5 |
| 126 | 136 | 1FA |
| 127 | 139 | 200 |
| 128 | 13D | 205 |
| 129 | 140 | 20B |
| 130 | 144 | 211 |
| 131 | 147 | 217 |
| 132 | 14B | 21C |
| 133 | 14E | 222 |
| 134 | 152 | 228 |
| 135 | 156 | 22E |
| 136 | 15A | 234 |
| 137 | 15D | 23A |
| 138 | 161 | 241 |
| 139 | 165 | 247 |
| 140 | 169 | 24D |
| 141 | 16D | 254 |
| 142 | 171 | 25A |
| 143 | 175 | 261 |
| 144 | 179 | 267 |
| 145 | 17D | 26E |
| 146 | 181 | 275 |
| 147 | 186 | 27C |
| 148 | 18A | 283 |
| 149 | 18E | 28A |
| 150 | 193 | 291 |
| 151 | 197 | 298 |
| 152 | 19C | 29F |
| 153 | 1A0 | 2A6 |
| 154 | 1A5 | 2AE |
| 155 | 1A9 | 2B5 |
| 156 | 1AE | 2BD |
| 157 | 1B3 | 2C4 |
| 158 | 1B8 | 2CC |
| 159 | 1BD | 2D4 |
| 160 | 1C2 | 2DC |
| 161 | 1C7 | 2E4 |
| 162 | 1CC | 2EC |
| 163 | 1D1 | 2F4 |
| 164 | 1D6 | 2FC |
| 165 | 1DB | 305 |
| 166 | 1E0 | 30D |
| 167 | 1E6 | 315 |
| 168 | 1EB | 31E |
| 169 | 1F1 | 327 |
| 170 | 1F6 | 32F |
| 171 | 1FC | 338 |
| 172 | 202 | 341 |
| 173 | 207 | 34A |
| 174 | 20D | 354 |
| 175 | 213 | 35D |
| 176 | 219 | 366 |
| 177 | 21F | 370 |
| 178 | 225 | 379 |
| 179 | 22C | 383 |
| 180 | 232 | 38D |
| 181 | 238 | 397 |
| 182 | 23F | 3A1 |
| 183 | 245 | 3AB |
| 184 | 24C | 3B5 |
| 185 | 253 | 3BF |
| 186 | 259 | 3CA |
| 187 | 260 | 3D4 |
| 188 | 267 | 3DF |
| 189 | 26E | 3EA |
| 190 | 276 | 3F5 |
| 191 | 27D | 400 |
| 192 | 284 | 40B |
| 193 | 28C | 416 |
| 194 | 293 | 422 |
| 195 | 29B | 42D |
| 196 | 2A2 | 439 |
| 197 | 2AA | 444 |
| 198 | 2B2 | 450 |
| 199 | 2BA | 45C |
| 200 | 2C2 | 469 |
| 201 | 2CB | 475 |
| 202 | 2D3 | 481 |
| 203 | 2DC | 48E |
| 204 | 2E4 | 49B |
| 205 | 2ED | 4A7 |
| 206 | 2F6 | 4B4 |
| 207 | 2FF | 4C1 |
| 208 | 308 | 4CF |
| 209 | 311 | 4DC |
| 210 | 31B | 4EA |
| 211 | 324 | 4F7 |
| 212 | 32E | 505 |
| 213 | 338 | 513 |
| 214 | 341 | 521 |
| 215 | 34B | 530 |
| 216 | 356 | 53E |
| 217 | 360 | 54D |
| 218 | 36B | 55B |
| 219 | 375 | 56A |
| 220 | 380 | 57A |
| 221 | 38B | 589 |
| 222 | 396 | 598 |
| 223 | 3A2 | 5A8 |
| 224 | 3AD | 5B8 |
| 225 | 3B9 | 5C8 |
| 226 | 3C5 | 5D8 |
| 227 | 3D1 | 5E8 |

-continued

| index | LED dac hex | LED fraction 0.12 binary 12 bit hex |
|---|---|---|
| 228 | 3DD | 5F8 |
| 229 | 3E9 | 609 |
| 230 | 3F6 | 61A |
| 231 | 403 | 62B |
| 232 | 410 | 63C |
| 233 | 41D | 64D |
| 234 | 42A | 65F |
| 235 | 438 | 671 |
| 236 | 446 | 683 |
| 237 | 454 | 695 |
| 238 | 462 | 6A7 |
| 239 | 471 | 6BA |
| 240 | 480 | 6CC |
| 241 | 48F | 6DF |
| 242 | 49E | 6F3 |
| 243 | 4AE | 706 |
| 244 | 4BE | 71A |
| 245 | 4CE | 72D |
| 246 | 4DE | 741 |
| 247 | 4EF | 756 |
| 248 | 500 | 76A |
| 249 | 511 | 77F |
| 250 | 523 | 794 |
| 251 | 535 | 7A9 |
| 252 | 547 | 7BE |
| 253 | 55A | 7D4 |
| 254 | 56D | 7E9 |
| 255 | 580 | 800 |
| 256 | 594 | 816 |
| 257 | 5A8 | 82C |
| 258 | 5BC | 843 |
| 259 | 5D1 | 85A |
| 260 | 5E6 | 871 |
| 261 | 5FC | 889 |
| 262 | 612 | 8A1 |
| 263 | 628 | 8B9 |
| 264 | 63F | 8D1 |
| 265 | 656 | 8EA |
| 266 | 66E | 903 |
| 267 | 686 | 91C |
| 268 | 69F | 935 |
| 269 | 6B8 | 94F |
| 270 | 6D2 | 969 |
| 271 | 6EC | 983 |
| 272 | 707 | 99D |
| 273 | 722 | 9B8 |
| 274 | 73E | 9D3 |
| 275 | 75B | 9EF |
| 276 | 778 | A0A |
| 277 | 796 | A26 |
| 278 | 7B4 | A43 |
| 279 | 7D3 | A5F |
| 280 | 7F3 | A7C |
| 281 | 813 | A99 |
| 282 | 834 | AB7 |
| 283 | 856 | AD5 |
| 284 | 879 | AF3 |
| 285 | 89C | B12 |
| 286 | 8C0 | B30 |
| 287 | 8E5 | B50 |
| 288 | 90B | B6F |
| 289 | 931 | B8F |
| 290 | 959 | BAF |
| 291 | 981 | BD0 |
| 292 | 9AB | BF1 |
| 293 | 9D5 | C12 |
| 294 | A00 | C34 |
| 295 | A2D | C56 |
| 296 | A5A | C78 |
| 297 | A89 | C9B |
| 298 | AB8 | CBE |
| 299 | AE9 | CE1 |
| 300 | B1B | D05 |
| 301 | B4E | D2A |
| 302 | B82 | D4E |
| 303 | BB8 | D73 |
| 304 | BEF | D99 |
| 305 | C27 | DBF |
| 306 | C61 | DE5 |
| 307 | C9C | E0C |
| 308 | CD9 | E33 |
| 309 | D17 | E5B |
| 310 | D57 | E83 |
| 311 | D98 | EAB |
| 312 | DDB | ED4 |
| 313 | E20 | EFD |
| 314 | E67 | F27 |
| 315 | EAF | F51 |
| 316 | EFA | F7C |
| 317 | F46 | FA7 |
| 318 | F94 | FD3 |
| 319 | FE5 | FFF |

The same formula and method may be used to generate red gain values or green gain values. The red gain values or green gain values may also be saved in a light source control table. In addition to adding pre-calculated color gains to the light source control tables, the correction values may be calculated in real time using the above formula as the light source drive current is altered.

There is disclosed in the above description and the drawings, an endoscope illumination system and method which overcomes the disadvantages associated with the prior art. However, it will be apparent that variations and modifications of the disclosed embodiments may be made without departing from the principles of the invention. The presentation of the preferred embodiments herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. §112.

What is claimed is:

1. A method for color correction in a camera system having a camera, a light source and a controller, the method comprising:
   setting a first light source drive current level;
   performing a first white balance operation and obtaining at least one of red gain, blue gain and green gain values corresponding to the first light source drive current level;
   setting a second light source drive current level different than the first light source drive current level;
   performing a second white balance operation and obtaining at least one of red gain, blue gain and green gain values corresponding to the second light source drive current level; and
   determining a relationship between light source current levels and at least one of red gain, blue gain and green gain values using the obtained at least one of red gain, blue gain and green gain values corresponding to the first and second light source drive current levels.

2. The method of claim 1 wherein the first light source drive current level and the second light source drive current level are selected from the group consisting of 25%, 50%, 75% and 100%.

3. The method of claim 1 further comprising the steps of:
setting a third light source drive current level different than the first light source drive current level and the second light source drive current level; and
performing a third white balance operation and obtaining at least one of red gain, blue gain and green gain values corresponding to the third light source drive current level.

4. The method of claim 1 wherein after the step of setting a first light source drive current level the method further comprises the step of waiting a predetermined time.

5. The method of claim 4 wherein the step of waiting a predetermined time further comprises waiting for at least one video frame to elapse.

6. The method of claim 4 wherein after the step of setting a second light source drive current level the method further comprises the step of waiting a predetermined time.

7. The method of claim 6 wherein the step of waiting a predetermined time further comprises waiting for at least one video frame to elapse.

8. The method of claim 1 wherein the light source is a white light emitting diode.

9. The method of claim 8 wherein the step of determining a relationship between light source current levels and at least one of red gain, blue gain and green gain values comprises the step of determining a relationship between light source current levels and blue gain values.

10. The method of claim 1 further comprising the step of generating a light source control table comprising at least one of a red gain value, a blue gain value and a green gain value for each light source drive current level.

11. The method of claim 10 wherein the light source is a white light emitting diode and the step of generating a light source control table comprises generating a blue gain value for each light source drive current level.

12. The method of claim 1 further comprising the step of receiving a white balance request.

13. A system for color correction in an endoscopic camera system comprising:
an imaging device for taking images;
an illumination system for providing light for the imaging device;
a camera control unit that processes images from the imaging device, the camera control unit further comprising:
an illumination controller;
a processor in communication with the illumination controller; and
a memory in communication with the processor;
wherein the camera control unit is configured to receive a white balance request; set a first light source drive current level; perform a first white balance operation and obtain at least one of red gain, blue gain and green gain values corresponding to the first light source drive current level; set a second light source drive current level different than the first light source drive current level; perform a second white balance operation and obtain at least one of red gain, blue gain and green gain values corresponding to the second light source drive current level; determine a relationship between light source current levels and at least one of red gain, blue gain and green gain values using the obtained at least one of red gain, blue gain and green gain values corresponding to the first and second light source drive current levels; and store the determined relationship between light source current levels and at least one of red gain, blue gain and green gain values to the memory.

14. The method of claim 13 wherein the first light source drive current level and the second light source drive current level are selected from the group consisting of 25%, 50%, 75% and 100%.

15. The system of claim 13 wherein the camera control unit is further configured to set a third light source drive current level different than the first light source drive current level and the second light source drive current level; and perform a third white balance operation and obtain at least one of red gain, blue gain and green gain values corresponding to the third light source drive current level.

16. The system of claim 13 wherein the light source is a white light emitting diode.

17. The system of claim 13 wherein the camera control unit is further configured to generate a light source control table comprising at least one of a red gain value, a blue gain value and a green gain value for each light source drive current level.

* * * * *